(12) United States Patent
Bottaro et al.

(10) Patent No.: US 6,303,774 B1
(45) Date of Patent: Oct. 16, 2001

(54) NUCLEOSIDE PYROPHOSPHATE AND TRIPHOSPHATE ANALOGS AND RELATED COMPOUNDS

(75) Inventors: Jeffrey C. Bottaro, Mountain View; Robert J. Schmitt, Palo Alto; Mark A. Petrie, Cupertino; Paul E. Penwell, Palo Alto, all of CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 09/334,069

(22) Filed: Aug. 20, 1999

(51) Int. Cl.$^7$ .................................................. C07H 19/20
(52) U.S. Cl. ........................... 536/26.23; 536/26.26; 536/26.7; 536/26.8
(58) Field of Search .............................. 536/26.23, 26.26, 536/26.7, 26.8; 514/47, 48, 51

(56) References Cited

U.S. PATENT DOCUMENTS

| | | | |
|---|---|---|---|
| 3,701,772 | * 10/1972 | Tamura et al. | 536/26.23 |
| 3,846,402 | 11/1974 | Eckstein et al. | |
| 4,266,048 | * 5/1981 | Horwitz et al. | 536/26.3 |
| 4,728,730 | * 3/1988 | Frey et al. | 536/26.26 |
| 4,981,957 | * 1/1997 | Lebleu et al. | 536/25.2 |
| 5,118,672 | * 6/1992 | Schinazi et al. | 514/47 |
| 5,166,330 | * 11/1992 | Engels et al. | 536/26.7 |
| 5,194,599 | * 3/1993 | Froehler et al. | 536/26.72 |
| 5,374,626 | * 12/1994 | Battistini et al. | 514/47 |
| 5,401,725 | * 3/1995 | Kawanaka et al. | 514/47 |
| 5,492,898 | * 2/1996 | Bertics et al. | 514/47 |
| 5,495,009 | * 2/1996 | Matteucci et al. | 536/25.3 |
| 5,516,762 | * 5/1996 | Bertics et al. | 514/47 |
| 5,565,555 | * 10/1996 | Froehler et al. | 536/26.22 |
| 5,614,504 | * 3/1997 | Hadden et al. | 514/45 |
| 5,624,913 | * 4/1997 | Proctor et al. | 514/47 |
| 5,684,148 | * 11/1997 | Caruthers et al. | 536/26.1 |
| 5,721,219 | * 2/1998 | Ingall et al. | 514/47 |
| 5,789,576 | * 8/1998 | Daily et al. | 536/25.6 |

FOREIGN PATENT DOCUMENTS

| | | |
|---|---|---|
| 889305 | * 12/1971 | (CA) . |
| 277462 | * 4/1990 | (DE) . |
| 277463 | * 4/1990 | (DE) . |
| 0467183 | * 1/1992 | (EP) . |
| 0485232 | 5/1992 | (EP) . |
| 58126872 | * 7/1983 | (JP) . |
| 9306120 | * 4/1993 | (WO) . |
| WO 96/00733 | 1/1996 | (WO) . |
| 0006145 | * 2/2000 | (WO) . |
| 0020382 | * 4/2000 | (WO) . |

OTHER PUBLICATIONS

Heinze et al., "Zur Kenntnis des Trimeren Sulfimids, $(O_2SNH)_3$," *Zeitschrift für Anorganische und Allgemeine Chemie*, 275(1–3), 49–58 (Feb.,1954).*

Mandell et al., "Ammonolysis of Perchloryl Fluoride," *Journal of Inorganic and Nuclear Chemistry*, 12, 90–94 (1959); originally presented before Div. of Ind. Engnr. Chem. of the Amer. Chem. Soc., Sep. 11, 1958).*

Beard et al., "Reactions of Dichlorine Heptoxide with Amines," *Journal of the American Chemical Society*, 96(10), 3237–3239 (May 15, 1974).*

Jennings et al., "Synthesis of Analogues of 5–Iodo–2'–deoxyuridine–5'–diphosphate," *Journal Chemical Society(GB), Perkin Trans. I*, (Issue No. 17), 2197–2202 (1992).*

Baschang et al. (1973), "Imidophosphate als Neue Necleotid–Derivate," *Angew. Chem.* 85(1):43–44.

* cited by examiner

*Primary Examiner*—Gary Geist
*Assistant Examiner*—L E Crane
(74) *Attorney, Agent, or Firm*—Dianne E. Reed; Reed & Associates

(57) ABSTRACT

Novel compounds are provided in the form of nucleoside pyrophosphate and triphosphate analogs. In these analogs, the pyrophosphate or triphosphate group is replaced with a moiety that is isosterically and electronically identical thereto, but is hydrolytically and enzymatically more stable. The compounds are useful as therapeutic agents, e.g., as antiviral agents, anticancer agents, metabolic moderators and the like. The invention also provides pharmaceutical compositions containing a compound of the invention as an active agent, and in addition provides methods of treating disease, including viral infections, cancer, bacterial infections, inflammatory and/or autoimmune diseases, and the like, by administering a compound of the invention to a patient in need of such treatment.

50 Claims, No Drawings

NUCLEOSIDE PYROPHOSPHATE AND TRIPHOSPHATE ANALOGS AND RELATED COMPOUNDS

TECHNICAL FIELD

The present invention provides novel compounds that are useful as therapeutic agents, e.g., as antiviral agents, anticancer agents and metabolic moderators. The invention additionally relates to pharmaceutical compositions containing a compound of the invention as the active agent and to methods of using the novel compounds as therapeutic agents. The invention has application in the fields of biochemistry and medicinal chemistry and particularly provides nucleoside pyrophosphate and triphosphate analogs and related compounds for use in the treatment of disease.

BACKGROUND

Nucleotides are some of the most ubiquitous compounds in nature, one example of which is the adenosine triphosphate ("ATP") molecule shown below:

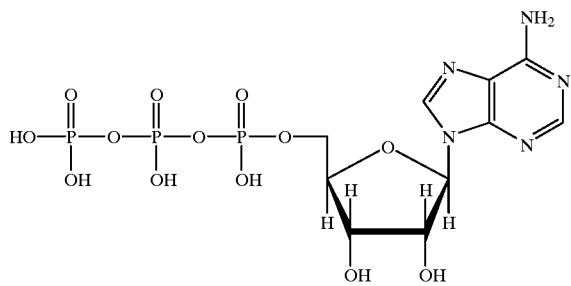

The four principal ribonucleotide triphosphates may be polymerized to provide "RNA," or "ribonucleic acid." In addition to its role in all normal cells, RNA represents the genetic material of one major class of pathogenic viruses known as the RNA viruses, examples of which are HIV and herpes viruses. When the sugar moiety is deoxyribose, the four principal deoxyribonucleotide triphosphates are polymerized into deoxyribonucleic acid strands, or "DNA," the genetic material of all plants and animals. There is also another class of pathogenic viruses known as DNA viruses, examples of which include measles and mumps.

Much of the cell's chemistry with regard to these various nucleotide compounds involves the addition, removal or transfer of one or more of the phosphates groups within the triphosphate moiety, as illustrated by the equilibrium transphosphorylation reaction wherein a phosphate group is transferred between uridine diphosphate ("UDP") and ATP to give uridine triphosphate ("UIp") and adenosine diphosphate ("ADP"):

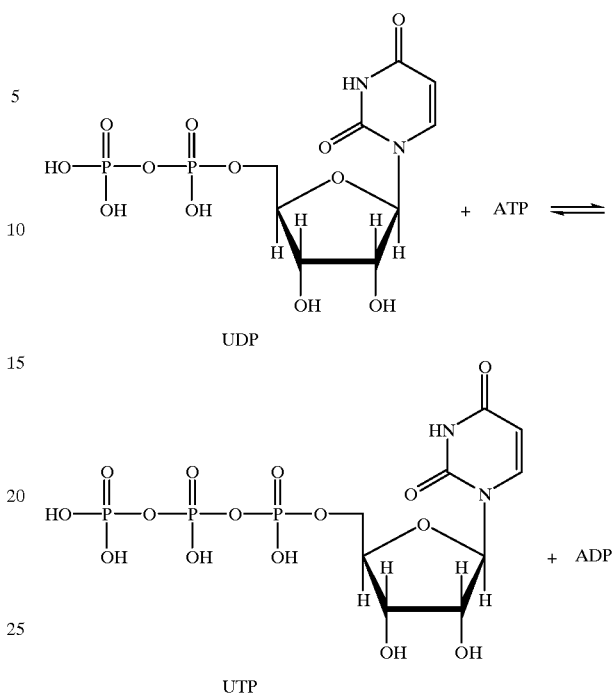

The body triphosphorylates and dephosphorylates drug and metabolic intermediates at extremely high rates, resulting in a constant low level of triphosphorylated materials that are then used in cellular processes. Phosphates, pyrophosphates and triphosphates of antiviral drugs, nucleosides, inositol, isoprenoids, and other biochemical building blocks are critical intermediates in the biosynthesis of nucleosides, proteins and hormones.

In spite of the presence of phosphorylated compounds throughout the body, such compounds are elusive as pharmacological candidates due to the hydrolytic lability of the pyrophosphate and triphosphate groups and their short half-lives in the bloodstream. Thus, there is a need in the art for functionally equivalent compounds, i.e., compounds that are isosterically and electronically identical to the natural pyrophosphates and triphosphates, but that are hydrolytically and enzymatically more stable, and preferably have reduced toxicity as well.

The present invention is addressed to the aforementioned need in the art, and provides an unprecedented class of nucleoside-based therapeutic agents containing a functional group that is isosterically and electronically identical to a natural pyrophosphate or triphosphate group, wherein the agents are hydrolytically and enzymatically more stable than the "natural" pyrophosphate and triphosphate compounds. The therapeutic agents now provided are useful in a variety of contexts, e.g., as antiviral agents, anticancer agents, metabolic moderators, and the like. The novel compounds are also useful as starting materials or intermediates in the synthesis of other nucleoside-based therapeutic agents, as research tools for studying nucleoside triphosphates and pyrophosphates (the naturally occurring compounds hydrolyze readily, resulting in inconvenience in the laboratory), and in the sequential preparation of oligonucleotides and polynucleotides of interest.

SUMMARY OF THE INVENTION

In one aspect of the invention, novel compounds are provided having the structure of formula (I)

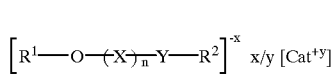
(I)

wherein:

x and y are integers in the range of 1 to 3 inclusive;

$R^1$ is a purine or pyrimidine base bound to a cyclic or acyclic sugar moiety, and may represent a single nucleoside or a nucleoside monomer contained within an oligonucleotide chain, wherein $R^1$ is bound through either its 3' or 5' position;

$R^2$ is selected from the group consisting of $N^-$—$ClO_3$, $N^-$—$NO_2$ and $N^-$—$SO_2R^3$ wherein $R^3$ is lower alkyl, halogenated lower alkyl, halo or amino;

X is
—$X^1$—$X^2$— or —$X^3$=N—;

$X^1$ and Y are independently selected from the group consisting of

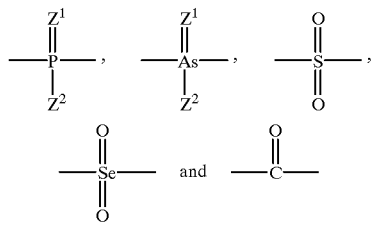

wherein $Z^1$ is selected from the group consisting of O, S, $C(CN)_2$, $NClO_3$, $N$—$NO_2$, $N$—$SO_3$ and $N$—$SO_2R^3$, and $Z^2$ is selected from the group consisting of $O^-$, $S^-$, lower alkyl, halogenated lower alkyl, halo, $BH_3^-$, $N^-$—$ClO_3$, $N^-$—$NO_2$ and $N^-$—$SO_2R^3$, with the proviso that when $R^2$ is $N^-$—$ClO_3$, then Y is other than

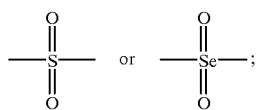

$X^2$ is selected from the group consisting of O, S and $N^-$; $X^3$ is

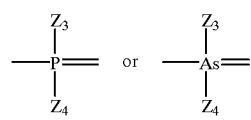

wherein $Z^3$ and $Z^4$ are independently selected from the group consisting of $O^-$, $S^-$, lower alkyl, halogenated lower alkyl, halo, $BH_3^-$, $N^-ClO_3$, $N^-$—$NO_2$ and $N^-$—$SO_2R^3$;

n is 0, 1 or 2, wherein when n is 2, the two X moieties may be the same or different; and Cat is a cationic species.

In a related aspect of the invention, novel nucleoside based compounds are provided having the structure of formula (II)

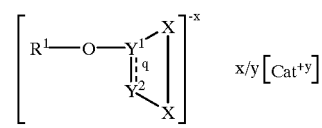
(II)

wherein $R^1$, x, y and Cat are as defined above with respect to formula (I), the X moieties may be the same or different and are as defined above with respect to formula (I), q is an optional double bond, $Y^1$ is $P=Z^1$, $As=Z^1$, $S=O$ or $Se=O$, and $Y^2$ is N, $N^-$, O or S, and further wherein (a) when $y^1$ is $S=O$ or $Se=O$, then q is a double bond and $Y^2$ is N, and (b) when $Y^1$ is $P=Z^1$ or $As=Z^1$, then q is absent and $Y^2$ is $N^-$, O or S. Depending on the definition of each "X" moiety, structures of formula (II) may be represented by any of the following subgeneric formulae (IIa) through (IId)

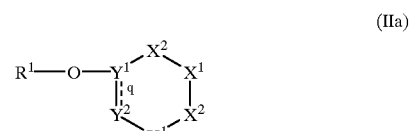
(IIa)

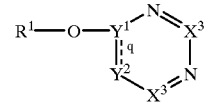
(IIb)

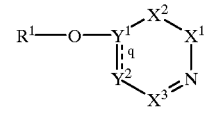
(IIc)

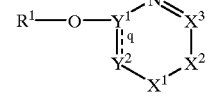
(IId)

in which $X^1$, $X^2$, $X^3$, $Y^1$, $Y^2$ and q are as defined previously, and wherein each structure bears a negative charge −x and is associated with x/y cationic moieties each bearing a positive charge +y.

In other aspects of the invention, novel compounds are provided that serve as starting materials or intermediates in the synthesis of compounds of formulae (I) and (II), and which are themselves useful as therapeutic agents. Such compounds have the structural formulae (III) and

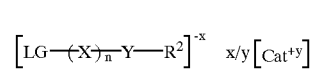
(III)

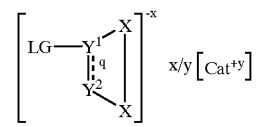
(IV)

wherein X, Y, $Y^1$, $Y^2$, $R^2$, Cat, n, x, y and q are as defined earlier, and LG is a leaving group displaceable by a nucleophile. For example, LG may be halo, displaceable by an alcohol ROH in the presence of base.

Other such compounds of the invention may be more generally represented by formulae (V) and (VI)

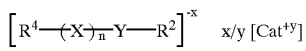
(V)

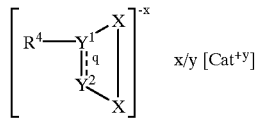
(VI)

which are identical to the compounds of formulae (III) and (IV) except that LG has been replaced with the substituent $R^4$, which is a substituted or unsubstituted hydrocarbyl group of 1 to 24 carbon atoms, or, alternatively, a moiety defined as for $R^2$, i.e., selected from the group consisting of $N^-$—$ClO_3$, $N^-$—$NO_2$ and $N^-SO_2R^3$, with the proviso that when $R^4$ is $N^-ClO_3$, $Y^1$ is other than S=O or Se=O.

The invention is also directed to pharmaceutical compositions containing a novel compound as provided herein, in combination with a pharmaceutically acceptable carrier. Preferably, such compositions are oral dosage forms and thus contain a carrier suitable for oral drug administration.

In addition, the invention provides methods of using a compound of the invention as a therapeutic agent. The compounds are useful as antiviral agents, anticancer agents, metabolic moderators, and the like, and can thus be administered to treat a variety of conditions, disorders and diseases. A primary use of the compounds, however, is in treating individuals suffering from a viral infection.

DETAILED DESCRPTION OF THE INVENTION
Definitions and Nomenclature

It is to be understood that unless otherwise indicated, this invention is not limited to specific molecular structures, pharmaceutical compositions, methods of drug administration, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a novel compound" in a pharmaceutical composition means that more than one of the novel compounds can be present in the composition, reference to "a pharmaceutically acceptable carrier" includes combinations of such carriers, and the like. Similarly, reference to "a substituent" as in a compound substituted with "a substituent" includes the possibility of substitution with more than one substituent, wherein the substituents may be the same or different.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms. The term "cycloalkyl" as used herein refers to a cyclic hydrocarbon of from 3 to 8 carbon atoms, such as cyclopropyl, cyclobutyl, cyclopentyl, cyclohexyl, cycloheptyl and cyclooctyl.

The term "alkoxy" as used herein intends an alkyl group bound through a single, terminal ether linkage; that is, an "alkoxy" group may be defined as —O-alkyl where alkyl is as defined above. A "lower alkoxy" group intends an alkoxy group containing one to six, more preferably one to four, carbon atoms.

The term "aryl" as used herein, and unless otherwise specified, refers to an aromatic species containing 1 to 3 aromatic rings, either fused or linked, and either unsubstituted or substituted with 1 or more substituents typically selected from the group consisting of lower alkyl, lower alkoxy, halogen, and the like. Preferred aryl groups contain 1 aromatic ring or 2 fused or linked aromatic rings. The term "arylene" refers to a difunctional aromatic species containing 1 to 3 aromatic rings substituted with 1 or more substituents as above. Preferred arylene substituents contain 1 aromatic ring (e.g., phenylene) or 2 fused or linked aromatic rings (e.g., biphenylylene).

The term "halo" or "halogen" is used in its conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "hydrocarbyl" is used in its conventional sense to refer to a hydrocarbon group containing carbon and hydrogen, and may be aliphatic, alicyclic or aromatic, or may contain a combination of aliphatic, alicyclic and/or aromatic moieties. Aliphatic and alicyclic hydrocarbyl may be saturated or they may contain one or more unsaturated bonds, typically double bonds. The hydrocarbyl moieties herein generally contain 1 to 24 carbon atoms, more typically 1 to 12 carbon atoms, and may be substituted with various substituents or contain nonhydrocarbyl linkages, e.g., —O—, —S—, —$N^-$—, etc.

The term "substituent" as used herein refers to a functional group or nonhydrogen substituent bound to an atom of a molecular moiety herein. Those skilled in the art will appreciate that the compounds and molecular segments drawn and defined herein may be unsubstituted, substituted as specifically indicated, or substituted with other substituents. Examples of substituents which may be present in the compounds of the invention include, but are not limited to, halo, particularly chloro and fluoro; hydroxy; alkoxy, particularly lower alkoxy, such as methoxy, n-propoxy and t-butoxy; primary amino ($NH_2$); secondary amino, typically lower alkyl-substituted amino; tertiary amino, typically lower alkyl-disubstituted amino; nitro; acyloxy, which may be represented as R'COO—; acylamido, which may be represented as R'CONH— and thiol analogs thereof (R'CSO— and R'CSNH—, respectively), wherein R' is alkyl, typically lower alkyl; carboxy (—C(O)OH); alkoxycarbonyl (—C(O)OR'); carbamyl (—C(O)$NH_2$); alkylcarbamyl (C(O)NHR'); alkylsulfonyl (R'$SO_2$—); and alkylphosphonyl (R'P(OR')O—). For example, "substituted hydrocarbyl" refers to a "hydrocarbyl" group as defined above substituted with one or more, typically one to four, generally one or two, "substituents" as just defined, e.g., halo, alkoxy, amino, nitro or the like.

It will be appreciated that, as used herein, the term "nucleoside" will include those moieties which contain not only the known purine and pyrimidine bases, but also modified purine and pyrimidine bases and other heterocyclic bases which have been modified (these moieties are sometimes referred to herein, collectively, as "purine and pyrimidine bases and analogs thereof"). Such modifications include methylated purines or pyrimidines, acylated purines or pyrimidines, and the like. Modified nucleosides will also include modifications on the sugar moiety, e.g., wherein one or more of the hydroxyl groups are replaced with halogen, aliphatic groups, or are functionalized as ethers, amines, or the like, as will be discussed in detail elsewhere herein. The term "nucleoside" is also intended to encompass nucleoside monomers as well as nucleosides present within an oligonucleotide chain, either at a terminus thereof or within the oligonucleotide backbone.

As used herein, the term "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers containing normucleotidic backbones, providing that the polymers contain nucleobases in a configuration which allows for base pairing and base stacking, such as is found in DNA and RNA. The term "oligonucleotide" includes double- and single-stranded DNA, as well as double- and single-stranded RNA and DNA:RNA hybrids, and also include known types of modifications, for example, labels which are known in the art, methylation, "caps," and the like.

By "pharmaceutically acceptable carrier" is meant a material which is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmaceutically acceptable" salt of a novel compound as provided herein is a salt or ester which is not biologically or otherwise undesirable.

"Pharmaceutically or therapeutically effective dose or amount" refers to a dosage level sufficient to induce a desired biological result. That result can be alleviation of the signs, symptoms, or causes of a disease, or any other desired alteration of a biological system.

The term "treat" as in "to treat a disease" is intended to include any means of treating a disease in a mammal, including (1) preventing the disease, i.e., avoiding any clinical symptoms of the disease, (2) inhibiting the disease, that is, arresting the development or progression of clinical symptoms, and/or (3) relieving the disease, i.e., causing regression of clinical symptoms.

"Optional" or "optionally" means that the subsequently described circumstance may or may not occur, so that the description includes instances where the circumstance occurs and instances where it does not. For example, recitation of a double bond as "optionally present" encompasses both the molecular moiety containing the double bond and the molecular moiety not containing the double bond.

In the molecular structures herein, single bonds are indicated in the conventional sense using a single line connecting two atoms, while double bonds are indicated in the conventional sense using a double line between two adjacent atoms. However, it will be appreciated that molecular structures can be drawn in different ways, and that in some cases a particular bond may be drawn as either a single or double bond, with both representations being chemically accurate and indicating the same structure.

The Novel Compounds

In one embodiment, then, novel compounds are provided comprising nucleoside analogs having the general structure of formula (I)

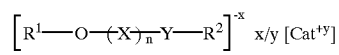
(I)

wherein the nucleoside is represented by $R^1$ as will be discussed in further detail below, n is 0, 1 or 2, x and y are integers in the range of 1 to 3 inclusive, and $R^2$, X, Y and Cat are defined as follows:

$R^2$ is selected from the group consisting of $N^-$—$ClO_3$, $N^-$—$NO_2$ and $N^-$—$SO_2R^3$ wherein $R^3$ is lower alkyl, halogenated lower alkyl, halo or amino, and a particularly preferred $R^2$ group is $N^-$—$ClO_3$.

X is
—$X^1$—$X^2$— or —$X^3$=N—;

$X^1$ and Y are independently selected from the group consisting of

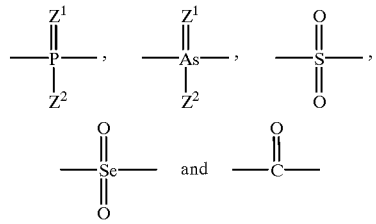

wherein $Z^1$ is selected from the group consisting of O, S, $C(CN)_2$, $NClO_3$, $N$—$NO_2$, $N$—$SO_3$ and $N$—$SO_2R^3$, and $Z^2$ is selected from the group consisting of $O^-$, $S^-$, lower alkyl, halogenated lower allyl, halo, $BH_3^-$, $N^-$—$ClO_3$, $N^-$—$NO_2$ and $N^-$—$SO_2R^3$, with the proviso that when $R^2$ is $N^-$—$ClO_3$, then Y is other than

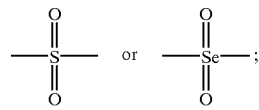

$X^2$ is selected from the group consisting of O, S and $N^-$; and
$X^3$ is

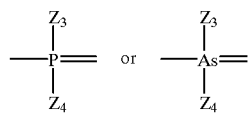

wherein $Z^3$ and $Z^4$ are independently selected from the group consisting of $O^-$, $S^-$, lower alkyl, halogenated lower alkyl, halo, $BH_3^-$, $N^-$—$ClO_3$, $N^-$—$NO_2$ and $N^-$—$SO_2R^3$.

Preferred $X^1$ and Y moieties are

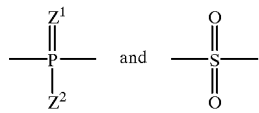

wherein, in the former linkage, $Z^1$ and $Z^2$ are defined previously, with particularly preferred $Z^1$ moieties selected from the group consisting of O, S, $C(CN)_2$, $NClO_3$, $N$—$SO_3$, $N$—$SO_2CH_3$ and $N$—$SO_2CF_3$, and particularly preferred $Z^2$ moieties selected from the group consisting of O⁻, S⁻, CH₃, F, Cl, N⁻—ClO₃, N⁻—SO₂CH₃ and N⁻—SO₂CF₃.

The preferred X³ moiety is

wherein $Z^3$ and $Z^4$ are as defined previously; particularly preferred $Z^3$ and $Z^4$ are halo or lower alkyl, e.g., chloro, fluoro, methyl, ethyl, and the like.

The moiety $R^1$ is a nucleoside optionally contained within an oligonucleotide chain, and comprises a purine or a pyrinidine base or an analog thereof bound to a cyclic or acyclic sugar moiety. $R^1$ is bound to the remainder of the molecule, i.e., the adjacent "Y" moiety shown in structural formula (I), through either its 3'-hydroxyl group or its 5'-hydroxyl group. The purine or pyrimidine base may be conventional, e.g., adenine (A), thymine (T), cytosine (C), guanine (G) or uracil (U), or a protected form thereof, e.g., wherein the base is protected with a protecting group such as acyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N⁶-methyladenine, N⁶-isopentyladenine, 2-methylthio-N⁶-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methyguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, β-D-galactosylqueosine, β-D-mannosylqueosine, inosine, 1-methylinosine, hypoxanthine, xanthine, 2-aminopurine, 6-hydroxyaminopurine, 6-thiopurine and 2,6-diaminopurine. The sugar moiety conjugated to the purine or pyrimidine base may, is a monosaccharide which, as noted above, may be either cyclic or acyclic. Acyclic sugars typically contain 3–6 carbon atoms and include, for example, the acyclic sugar moieties present in acyclovir (—CH₂—O—CH₂CH₂—OH), ganciclovir (—CH₂—O—CH(CH₂OH)—CH₂—OH), and the like. Cyclic sugar moieties will generally be derived from furanose (a five-membered ring) or from pyranose (a six-membered ring), but more preferably from furanose forms. Examples of cyclic sugar moieties include threo-furanosyl (from threose, a four-carbon sugar), erythro-furanosyl (from rose, a four-carbon sugar), ribo-furanosyl (from ribose, a five-carbon sugar), arabino-furanosyl (from arabinose, a five-carbon sugar), and xylo-furanosyl (from xylose, a five-carbon sugar). Other suitable cyclic sugar moieties include "deoxy," "keto," and "dehydro" derivatives of the foregoing, and sugars substituted with amino groups, azide moieties, halogen substituents, aliphatic groups, and the like; examples of such modified sugar moieties are 2-ketopentofuranoses, 3-deoxyribose, 2,3-dideoxy-β-glycero-pent-2-enofuranosyl (as in stavudine), 2,3-dideoxy-2-azido-pentofiuranoyl (as in zidovudine, or "AZT"), and the like. Sugar moieties may be in any of their enantiomeric, diastereomeric or stereoisomeric forms, including, for example, D- or L-forms. It will be appreciated by those skilled in the art that numerous other sugar moieties may be employed in the context of the present invention.

The cationic moiety is typically a metal ion or an ammonium ion, either $NH_4^+$ or $NR_4^+$ wherein R is typically $C_1$–$C_{10}$ alkyl. Suitable metal ions include, for example, $Na^+$, $K^+$, $Li^+$, $Mg^{+2}$, $Zn^{+2}$, $Cs^+$, etc.

In preferred compounds, "n" is 0, so that the compound is a pyrophosphate analog rather than a triphosphate analog.

A preferred group of compounds encompassed by the general structure of formula (I) may be represented by formula (VII)

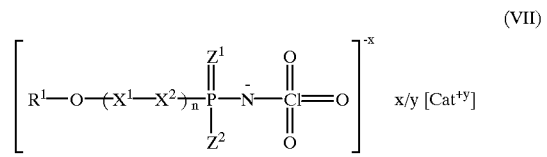

wherein when n is 1, the compounds are of the formula (VIII), while when n is 0, the compounds are of the formula (IX)

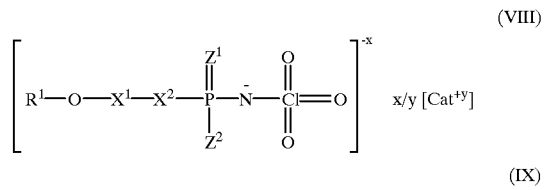

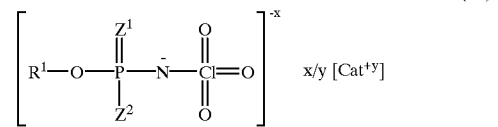

Within formula (VIII), particularly preferred compounds include, but are not limited to, structures of formulae (X) and (XI):

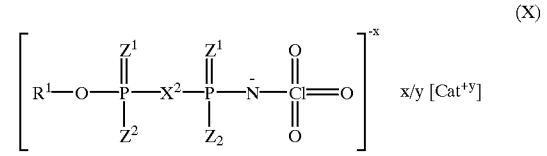

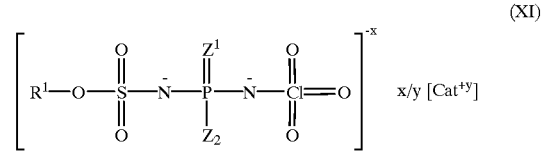

In all of the above structures, $R^1$, $R^2$, $X^1$, $X^2$, $Z^1$, $Z^2$, x y and C at are as defined previously.

Representative compounds encompassed by formula (I) thus include, but are not limited to, the following:

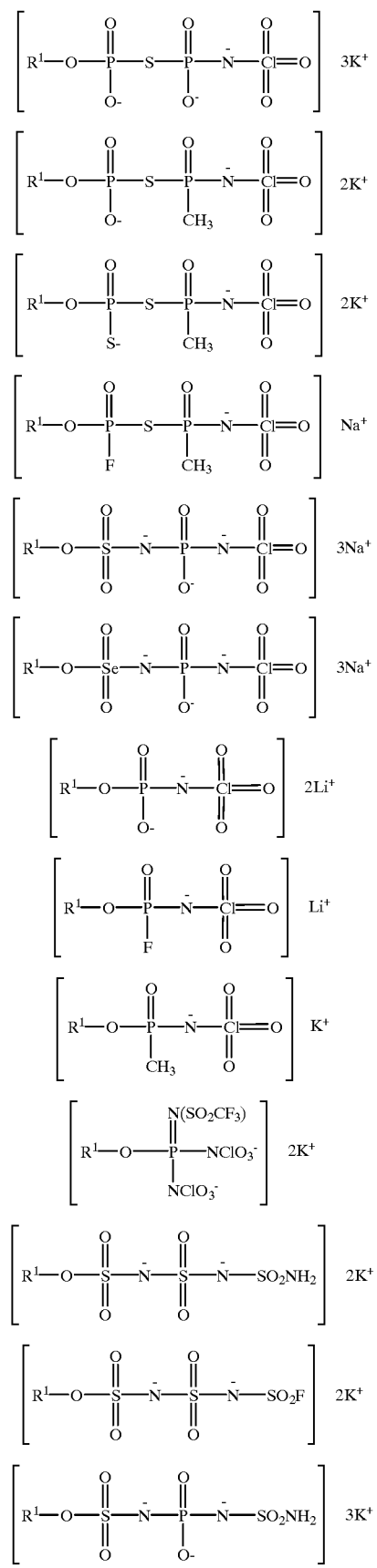

-continued

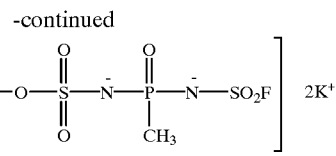

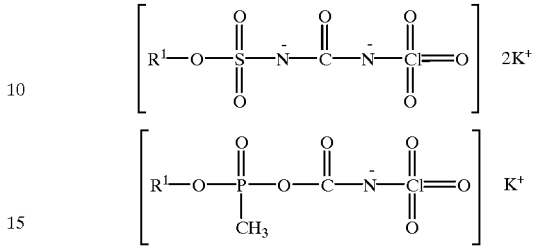

Other compounds of the invention that are nucleoside-based or incorporated in an oligonucleofide chain have the structural formula (II)

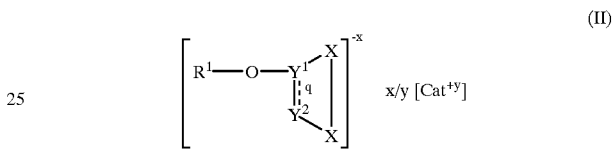

wherein $R^1$ is as defined above with respect to formula (I), the X moieties may be the same or different and are as defined above with respect to formula (I), q is an optional double bond, $Y^1$ is $P=Z^1$, $As=Z^1$, $S=O$ or $Se=O$, and $Y^2$ is N, $N^-$; O or S, and further wherein (a) when $Y^1$ is $S=O$ or $Se=O$, then q is a double bond and $Y^2$ is N, and (b) when $Y^1$ is $P=Z^1$ or $As=Z^1$, then q is absent and $Y^2$ is $N^-$, O or S. Generally, x and y are 1, 2 or 3, and $Cat^{+y}$ may be, for example, a metal ion (e.g., $Na^+$, $K^+$, $Li^+$, $Mg^{+2}$, $Zn^{+2}$, $Cs^+$, etc.) or an ammonium ion (e.g., $NH_4^+$ or $NR_4^+$ wherein R is $C_1$–$C_{10}$ alkyl). Since each X is either
—$X^1$—$X^2$— or —$X^3$ =N—, formula (II) encompasses four distinct subgeneric structures of formulae (IIa), (IIb), (IIc) and (IId)

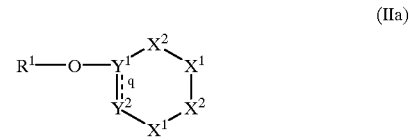

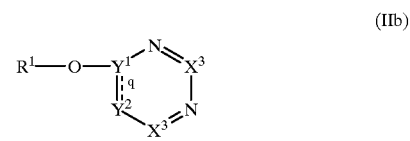

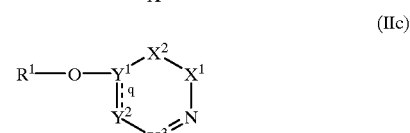

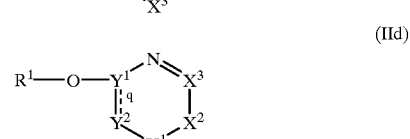

in which $X^1$, $X^2$, $X^3$, $Y^1$, $Y^2$ and q are as defined previously, and wherein the individual structures shown bear a negative charge −x and are associated with x/y cationic moieties $Cat^{+y}$. Examples of such compounds include, but are not limited to, the following:

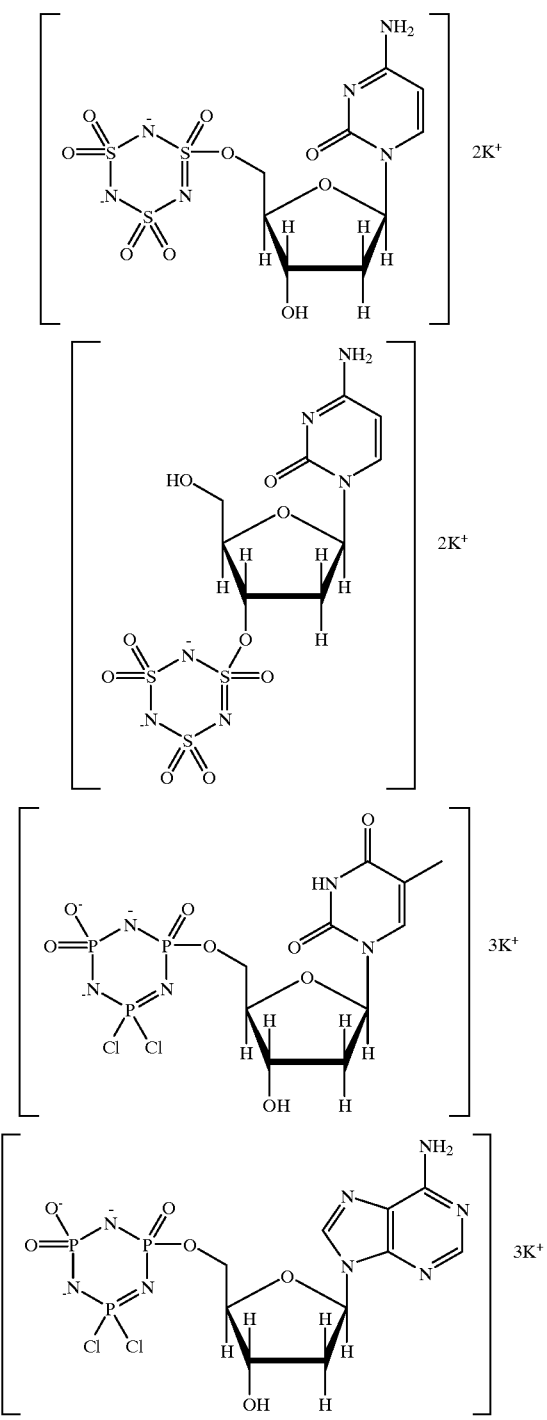

In a further embodiment, "free" anions not associated with a nucleoside are provided, which are useful to prepare compounds of structural formulae (I) and (II), and are themselves useful as therapeutic agents. One group of these compounds, shown in ionic association with a cationic moiety, has the structure of formula (III)

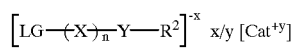
(III)

Another group of these compounds has the structural formal (IV)

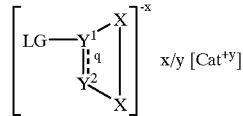
(IV)

Other preferred free anions of the invention may be more generally represented by formulae (V) and (VI)

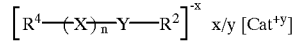
(V)

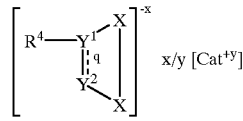
(VI)

which are identical to the compounds of formulae (III) and (IV) except that LG has been replaced with the substituent $R^4$, which is either substituted or unsubstituted $C_1$–$C_{24}$ hydrocarbyl or a moiety defined as for $R^2$, i.e., selected from the group consisting of $N^-$—$ClO_3$, $N^-$—$NO_2O$ and $N^-$—$SO_2R^3$, wherein when $R^4$ is $N^-$—$ClO_3$, then $Y^1$ is other than S═O or Se═O. If R4 is hydrocarbyl, any substituents may be present so long as the desired therapeutic activity is maintained and the resulting compounds are not in any way pharmacologically undesirable. Examples of substituents include, without limitation: halo, particularly chloro and fluoro; hydroxy; alkoxy, particularly lower alkoxy; amino; secondary amino, typically lower alkyl-substituted amino; tertiary amino, typically di(lower alkyl)-substituted amino; nitro; acyloxy, which may be represented as R'COO—; acylamido, which may be represented as R'CONH— and thiol analogs thereof (R'CSO— and R'CSNH—, respectively), wherein R' is alkyl, typically lower alkyl; carboxy (—C(O)OH); alkoxycarbonyl (—C(O)OR'); carbamyl (—C(O)NH₂); alkylcarbamyl (C(O)NHR'); alkylsulfonyl (R'SO₂—); and alkylphosphonyl (R'P(OR')O—), again, where R' is alkyl, typically lower alkyl, and may be substituted in a similar manner. Q may also contain nonhydrocarbyl linkages, e.g., —O—, —S—, —N═, —NR'—, and the like.

Representative compounds of structural formula (III), (IV), (V) and (VI) include, but are not limited to, the following:

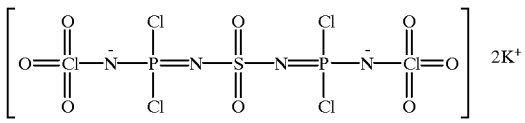

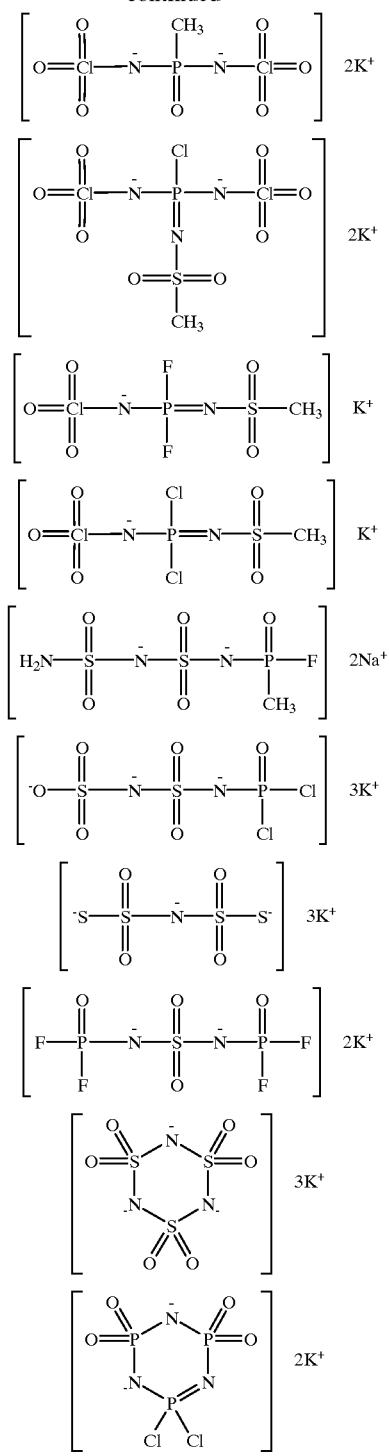

The compounds may be in the form of pharmaceutically acceptable salts or esters, or may be modified by appending one or more appropriate functionalities to enhance selected biological properties. Such modifications are known in the art and include those which increase biological penetration into a given biological system, increase oral bioavailability, increase solubility to allow administration by injection, and the like.

Salts of the compounds can be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). Acid addition salts are prepared from the free base (e.g., compounds having a neutral —NH$_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenusulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base.

Preferred acid addition salts of the present compounds are formed by association with an amine or polyamine that complexes with phosphate moieties or analogs thereof. The polyamine may be monomeric or polymeric, although preferred polyamines are the monomeric polyamines spermine, spermidine, putrescine, cadaverine and ethylenediamine, with spermine and spermidine particularly preferred.

Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures.

Certain of the novel compounds are chiral in nature and can thus be in enantiomerically pure form or in a racemic mixture. The invention is intended to encompass both the isomerically pure forms of the compounds shown and the racemic or diastereomeric mixtures thereof.

Utility

The compounds of the invention can be administered to mammalian individuals, including humans, as therapeutic agents. For example, the compounds of the invention are useful as antiviral agents, anticancer agents, antiproliferative agents, antibiotics, metabolic moderators, and the like.

Use as antiviral agents: The present invention provides a method for the treatment of a patient afflicted with a viral infection comprising administering to the patient a therapeutically effective antiviral amount of a compound of the invention. The term "viral infection" as used herein refers to an abnormal state or condition characterized by viral transformation of cells, viral replication and proliferation. Viral infections for which treatment with a compound of the invention will be particularly useful include: retroviruses such as, but not limited to, HTLV-I, HTLV-II, human immunodeficiency viruses, HTLV-III (AIDS virus), and the like;

RNA viruses such as, but not limited to, influenza type A, B, and C, mumps, measles, rhinovirus, dengue, rubella, rabies, hepatitis virus A, encephalitis virus, and the like; DNA viruses such as, but not limited to, herpes viruses (including herpes simplex virus-1, herpes simplex virus-2, varicella-zoster virus, Epstein-Barr virus, human cytomegalovirus, human herpes virus 6, human herpes virus 7, and human herpes virus 8), vaccinia, papilloma virus, hepatitis virus B, and the like. A "therapeutically effective antiviral amount" of a compound of the invention refers to an amount which is effective, upon single or multiple dose administration to the patient, in controlling the growth of the virus or in prolonging the survivability of the patient beyond that expected in the absence of such treatment. As used herein, "controlling the growth" of the virus refers to slowing, interrupting, arresting or stopping the viral transformation of cells or the replication and proliferation of the virus and does not necessarily indicate a total elimination of the virus.

Use as anticancer agents: The invention provides a method for using the compounds of the invention to treat cancer. In this embodiment, a patient afflicted with or susceptible to a neoplastic disease state is given a therapeutically effective antineoplastic amount of a compound of the invention. The term "neoplastic disease state" as used herein refers to an abnormal state or condition characterized by rapidly proliferating cell growth or neoplasm. Neoplastic disease states for which treatment with a compound of the invention will be particularly useful include: leukemias such as, but not limited to, acute lymphoblastic, chronic lymphocytic, acute myloblastic and chronic mylocytic leukemias; carcinomas, such as, but not limited to, those of the cervix, oesophagus, stomach, small intestines, colon and lungs; sarcomas, such as, but not limited to, oesteroma, osteosarcoma, lepoma, liposarcoma, hemangioma and hemangiosarcoma; melanomas, including amelanotic and melanotic; and mixed types of neoplasias such as, but not limited to, carcinosarcoma, lymphoid tissue type, follicular reticulum, cell sarcoma and Hodgkins Disease. A therapeutically effective antineoplastic amount of a compound of the invention refers to an amount which is effective, upon single or multiple dose administration to the patient, in preventing or controlling the growth of a neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

Use to treat infectious diseases: The compounds of the invention are also useful as antibiotic agents to treat individuals suffering from an infectious disease. Examples of infectious diseases that the compounds are useful to treat include, but are not limited to: systemic bacterial infections such as bartonellosis, brucellosis, Campylobacter infection, Bacillary angiomatosis, gonococcemia, Legionnaires' disease, leptospirosis, listeriosis, lyme disease, melioidosis, meningococcemia, salmonellosis, syphilis, tularemia, typhoid fever, vibriosis and Yersinia infection; mycobacterial infections such as *M. avium/M. intracellulare* infections and tuberculosis; other bacterial infections such as actinomycosis, nocardiosis and Whipple's disease; fungal infections such as aspergillosis, blastomycosis, candidiasis, coccidioidomycosis, cryptococcosis, histoplasmosis, mucormycosis, paracoccidioidomycosis and sporotrichosis; parasitic infections such as amebiasis, babesiasis, Chagas' disease, leishmaniasis, malaria, *P. carinii* infection, strongyloidiasis, toxocariasis, toxoplasmosis and trichinosis; mycoplasmal infections; chlamydial infections such as lymphogranuloma venereum, psittacosis and *C. pneumoniae* infection; localized pyogenic infections such as appendicitis, cholangitis, cholecystitis, diverticulitis, osteomyelitis, sinusitis and suppurative thrombophlebitis; and intravascular infections such as bacterial aortitis, bacterial endocarditis and vascular catheter infection.

Use as antiproliferative agents: The compounds of the invention are also useful to treat inflammatory disorders, immunologically mediated disorders and/or skin conditions typically associated with hyperproliferation of skin cells. Such disorders and conditions include, for example: rheumatoid arthritis ("RA"), degenerative joint disease (also known as "DJD" and "osteoarthritis"); gout and pseudogout; juvenile rheumatoid arthritis ("JRA"), psoriasis; atopic dermatitis; contact dermatitis (also known as "allergic eczema") and further eczematous dermatitises; exfoliative dermatitis; seborrhoeic dermatitis; dermatomyositis; polymyositis; scleroderma; vasculitis; Lichen planus; Pemphigus; bullous Pemphigoid, epidermolysis bullosa, urticaria, angioedemas, vasculitides; erythemas (including erythema multiforme and erythema nodosum); cutaneous eospinphilias; lupus erythematoses, including systemic lupus erythematosus and discoid lupus erythematosis; and Alopecia areata.

Accordingly, the present invention includes pharmaceutical compositions comprising, as an active ingredient, at least one of the compounds of the invention in association with a pharmaceutical carrier. The compounds of this invention can be administered by oral, parenteral (intramuscular, intraperitoneal, intravenous (IV) or subcutaneous injection), topical, transdermal (either passively or using iontophoresis or electroporation), transmucosal (e.g., nasal, vaginal, rectal, or sublingual) or pulmonary (e.g., via dry powder inhalation) routes of administration or using bioerodible inserts and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating, agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Topical formulations will generally comprise ointments, creams, lotions, gels or solutions. Ointments will contain a conventional ointment base selected from the four recognized classes: oleaginous bases; emulsifiable bases; emulsion bases; and water-soluble bases. Lotions are preparations to be applied to the skin or mucosal surface without friction, and are typically liquid or semiliquid preparations in which solid particles, including the active agent, are present in a water or alcohol base. Lotions are usually suspensions of solids, and preferably, for the present purpose, comprise a liquid oily emulsion of the oil-in-water type. Creams, as known in the art, are viscous liquid or semisolid emulsions, either oil-in-water or water-in-oil. Topical formulations may also be in the form of a gel, i.e., a semisolid, suspension-type system, or in the form of a solution.

Finally, formulations of these drugs in dry powder form for delivery by a dry powder inhaler offer yet another means of administration. This overcomes many of the disadvantages of the oral and intravenous routes.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally, dosage levels of between 0.001 to 10 mg/kg of body weight daily are administered to mammals.

The novel compounds are also useful as starting materials or intermediates in the synthesis of other nucleoside-based therapeutic agents, as research tools for studying nucleoside triphosphates and pyrophosphates (the naturally occurring compounds hydrolyze readily, resulting in inconvenience in the laboratory), and in the sequential preparation of oligonucleotides and polynucleotides of interest.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All patents, patent applications, journal articles and other references mentioned herein are incorporated by reference in their entireties.

EXAMPLE 1

Synthesis of perchloramido methanephosphonyl chloride, potassium salt

Scheme 1

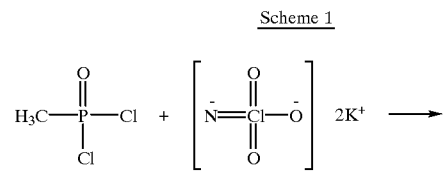

-continued

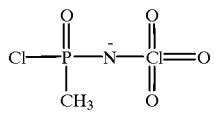

Dipotassium perchloramide (900 mg, 5 mmol) (synthesized according to the method of Mandell et al. (1959) *J Inorg. Nucl Chem.* 12:90–94) was suspended in 10 ml of dry acetonitrile, and was treated with 650 mg (5 mmol) of methanephosphonic dichloride while maintaining vigorous stirring. The mixture was stirred for 5 hours; a slow initial exotherm subsided after 1 hour. The mixture was then filtered through a 1"×½ plug of silica gel, eluting with 50 ml of acetonitrile. The effluent was concentrated in vacuo to a volume of 5 ml. This solution gave a TLC (acetonitrile/silica gel) peak with an $R_f$ of approximately 0.50. The identity of the product was confirmed using NMR spectroscopy. Other "free anions" of the invention may be synthesized in a similar manner.

EXAMPLE 2

Synthesis of the dipotassium salt of

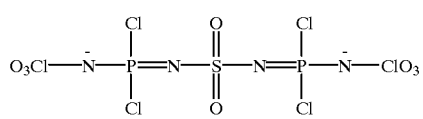

from sulfonyl bis(iminotrichlorophosphorane)

The above compound was prepared by reacting 5 mmol sulfonyl bis(iminotrichloro phosphorane)

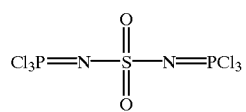

with 10 mmol $K_2NClO_3$ at room temperature for six hours. Filtration of KCl gave the desired product as an acetonitrile solution in greater than 90% yield, essentially pure as determined by TLC. Other analogous compounds of the invention may be synthesized in a similar manner.

EXAMPLE 3

Synthesis of the potassium salt of

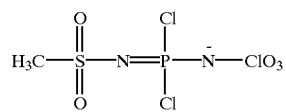

from methanesulfonyl(iminotrichlorphosphorane)

The above compound was prepared by reacting 5 mmol methanesulfonyl (iminotrichlorophosphorane)

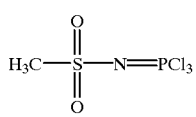

with 5 mmol $K_2NClO_3$ at room temperature for six hours. Filtration of KCl gave the desired product as an acetonitrile solution in greater than 90% yield. The identity of the product was confirmed using NMR spectroscopy. Similar compounds may be prepared using analogous reagents and reaction conditions.

EXAMPLE 4
Esterification of Alcohols

Scheme 2

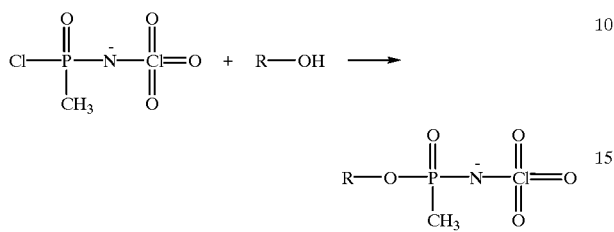

The alcohol R—OH (1 mmol) was dissolved in either dry acetonitrile (5 ml) or dry dimethylformamide (5 ml) and treated with 1 mmol each of perchloramido methanephosphonyl chloride, prepared in Example 1, and pyridine. The reaction mixture was stirred 15 hours and ion exchanged with potassium ions to remove pyridinium ions. The crude product was purified by column chromatography, eluting methanolic acetonitrile over silica gel. The reaction was carried using the following alcohols: methanol; benzyl alcohol; deoxyuridine; deoxyadenosine; and zidovudine (3'-azido-3'-deoxythymidine, or "AZT"). Yields were generally between 40% and 50%. All products were characterized using NMR spectroscopy.

EXAMPLE 5

The compounds of the invention may be evaluated in vitro as antiviral agents against human cytomegalovirus, as follows.

A suitable viral strain for the evaluation is Strain D-16 of HCMV. Continuous passaged MRC-5 cells may be obtained from the American Type Culture Collection (Bethesda, Md.) and used for testing herein, along with a growth medium consisting of Minimum Essential Medium (MEM) supplemented with 0.1% $NaHCO_3$ and 50 $\mu L$ gentamicin.

To a 96-well microtiter plate containing an established 24-hour monolayer of cells from which the medium is decanted is added 0.1 mL of varying (one-half $\log_{10}$) concentration of test compound, which incubates on the cell 15 minutes, after which 0.1 mL of virus in a concentration of 320 cell culture 50% infectious doses ($CCID_{50}$)/0.1 mL is added. The plate is covered with plastic wrap and incubated at 37° C. The cells are examined microscopically after 72 hours. The ED50 (the median effective antiviral dose, i.e., that dose which is effective in 50% of the cells), $CD_{50}$ (the median cytotoxic dose, i.e., that dose which produces cytotoxicity in 50% of the cells), and TI (the therapeutic index, meaning the ratio of the median cytotoxic dose and the median effective dose) are evaluated. The compounds are expected to provide acceptable values indicating their utility in treating CMV.

EXAMPLE 6

The compounds of the invention may be evaluated as therapeutic agents for the treatment of herpes simplex, as follows.

The eyes of a test mammal may be infected with a suspension of a selected strain of type I herpes simplex, for example, using the method of Jones et al., "Evaluation of Drug Effects in the Eye," *Symposium of the Royal Society of Medicine*, ed. Pigott (London: Association of Medical Advisors to the Pharmaceutical Industry, 1968), at pp. 83–97. One of the infected eyes is then treated topically beginning on the 4th day after infection with two drops of a 1% aqueous solution of a compound of the invention for a period of four days, dosing five times per day. On the fifth day after treatment, the treated infected eye will be free of infection whereas the non-treated eye will continue to exhibit the infection.

What is claimed is:

1. A compound having the structure of formula (I)

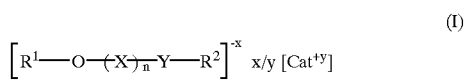

wherein:

x and y are integers in the range of 1 to 3 inclusive;

n is 0, 1 or 2, wherein when n is 2, the two X moieties may be the same or different;

Cat is a cationic species;

$R^1$ is a purine or pyrimidine base bound to a cyclic or acyclic sugar moiety, and may represent a single nucleoside or a nucleoside monomer contained within an oligonucleotide chain, wherein $R^1$ is bound through either its 3' or 5' position;

$R^2$ is selected from the group consisting of $N^-$—$ClO_3$, $N^-$—$NO_2$ and $N^-$—$SO_2R^3$ wherein $R^3$ is lower alkyl, halogenated lower alkyl, halo or amino;

X is
—$X^1$—$X^2$— or —$X^3$=N—;

$X^1$ and Y are independently selected from the group consisting of

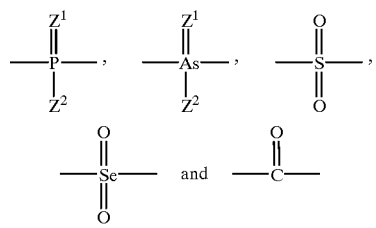

wherein $Z^1$ is selected from the group consisting of O, S, $C(CN)_2$, $NClO_3$, N—$NO_2$, N—$SO_3$ and N—$SO_2R^3$, and $Z^2$ is selected from the group consisting of $O^-$, $S^-$, lower alkyl, halogenated lower alky, halo, $BH_3^-$, $N^-$—$ClO_3$, $N^-$—$NO_2$ and $N^-$—$SO_2R^3$ [with the proviso that when $R^2$ is $N^-$—$ClO_3$, then Y is other than

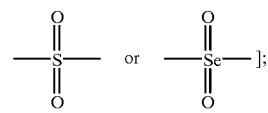

];

$X^2$ is selected from the group consisting of O, S and $N^-$; and $X^3$ is

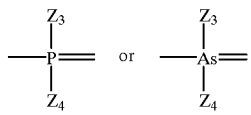

wherein
$Z^3$ and $Z^4$ are independently selected from the group consisting of $O^-$, $S^-$, lower alkyl, halogenated lower alkyl, halo, $BH_3^-$, $N^-$—$ClO_3$, $N^-$—$NO_2$ and $N^-$—$SO_2R^3$ with the proviso that when $R^2$ is $N^-$—$ClO_3$, then Y is other than

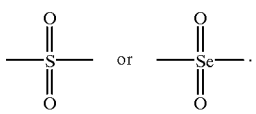

2. The compound of claim 1, wherein:

$R^1$ is a purine or pyrimidine base bound to a cyclic or acyclic sugar moiety;

$R^2$ is $N^-$—$ClO_3$;

X is
—$X^1$—$X^2$—
in which $X^1$ is

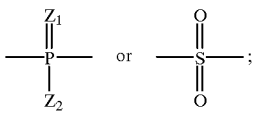

Y is

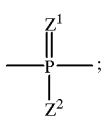

n is 0 or 1; and

Cat is a metal ion or an ammonium ion.

3. The compound of claim 2, wherein n is 1 and the compound has the structure of formula (VIII)

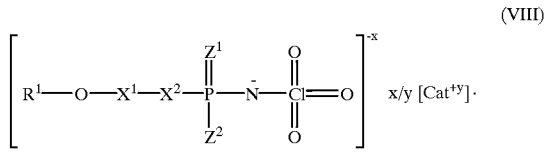

4. The compound of claim 3, having the structure of formula (X)

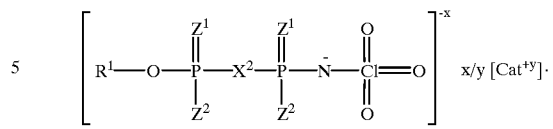

5. The compound of claim 3, having the structure of formula (XI)

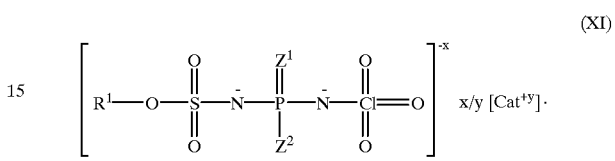

6. The compound of claim 2, wherein n is 0 and the compound has the structure of formula (IX)

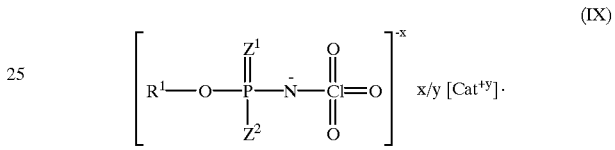

7. The compound of claim 1, wherein $R^1$ is a purine or pyrimidine base bound to a cyclic sugar moiety.

8. The compound of claim 7, wherein the cyclic sugar moiety is ribose or deoxyribose.

9. The compound of claim 8, wherein $R^1$ is attached at the 3' position of the cyclic sugar moiety.

10. The compound of claim 8, wherein $R^1$ is attached at the 5' position of the cyclic sugar moiety.

11. The compound of either one of claims 9 or 10, wherein $R^1$ is selected from the group consisting of adenosinyl, deoxyadenosinyl, guanosinyl, deoxyguanosinyl, cytidinyl, deoxycytidinyl, thymidinyl, uridinyl, inosinyl, deoxyinosinyl and dideoxyinosinyl.

12. A modified nucleoside having the structure

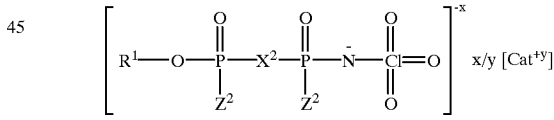

wherein:
$R^1$ is a nucleoside bound to the adjacent oxygen atom through its 5' carbon atom;
$X^2$ is selected from the group consisting of O, S and $N^-$;
the $Z^2$ are independently selected from the group consisting of $O^-$, $S^-$, $CH_3$, F, Cl, $N^-$—$ClO_3$, $N^-$—$SO_2CH_3$ and $N^-$—$SO_2CF_3$;
Cat is a cationic species selected from the group consisting of metal ions and ammonium ions; and
x and y are integers in the range of 1 to 3 inclusive.

13. The modified nucleoside of claim 12, wherein $X^2$ is O.

14. The modified nucleoside of claim 12, wherein $X^2$ is $N^-$.

15. The modified nucleoside of either claim 13 or claim 14, wherein both $Z^2$ are $O^-$.

16. The modified nucleoside of claim 12, wherein Cat is a metal ion.

17. The modified nucleoside of claim 15, wherein Cat is a metal ion.

18. The modified nucleoside of claim 16, wherein the metal ion is an alkali metal ion and x and y are 1.

19. The modified nucleoside of claim 17, wherein the metal ion is an alkali metal ion and x and y are 1.

20. The modified nucleoside of claim 18, wherein the alkali metal ion is sodium.

21. The modified nucleosiide of claim 18, wherein the alkali metal ion is potassium.

22. The modified nucleoside of claim 19, wherein the alkali metal ion is sodium.

23. The modified nucleoside of claim 19, wherein the alkali metal ion is potassium.

24. A modified nucleoside having the structure

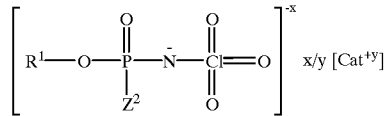

wherein:

R$^1$ is a nucleoside bound to the adjacent oxygen atom through its 5' carbon atom;

Z$^2$ is selected from the group consisting of O$^-$, S$^-$, CH$_3$, F, Cl, N$^-$—ClO$_3$, N$^-$—SO$_2$CH$_3$ and N$^-$—SO$_2$CF$_3$;

Cat is a cationic species selected from the group consisting of metal ions and ammonium ions; and x and y are integers in the range of 1 to 3 inclusive.

25. The modified nucleoside of claim 24, wherein Z$^2$ is selected from the group consisting of O$^-$ and CH$_3$.

26. The modified nucleoside of claim 25, wherein Z$^2$ is O$^-$.

27. The modified nucleoside of claim 25, wherein Z$^2$ is CH$_3$.

28. The modified nucleoside of claim 26, wherein Cat is a metal ion.

29. The modified nucleoside of claim 27, wherein Cat is a metal ion.

30. The modified nucleoside of claim 28, wherein the metal ion is an alkali metal ion and x and y are 1.

31. The modified nucleoside of claim 29, wherein the metal ion is an alkali metal ion and x and y are 1.

32. The modified nucleoside of claim 30, wherein the alkali metal ion is sodium.

33. The modified nucleoside of claim 30, wherein the alkali metal ion is potassium.

34. The modified nucleoside of claim 31, wherein the alkali metal ion is sodium.

35. The modified nucleoside of claim 32, wherein the alkali metal ion is potassium.

36. A modified nucleoside having the structure

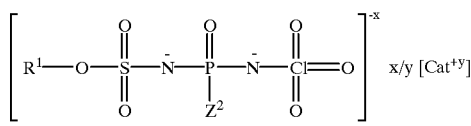

wherein:

R$^1$ is a nucleoside bound to the adjacent oxygen atom through its 5' carbon atom;

Z$^2$ is selected from the group consisting of O$^-$, S$^-$, CH$_3$, F, Cl, N$^-$—ClO$_3$, N$^-$—SO$_2$CH$_3$ and N$^-$—SO$_2$CF$_3$;

Cat is a cationic species selected from the group consisting of metal ions and ammonium ions; and x and y are integers in the range of 1 to 3 inclusive.

37. The modified nucleoside of claim 36, wherein Z$^2$ is selected from the group consisting of O$^-$ and CH$_3$.

38. The modified nucleoside of claim 37, wherein Z$^2$ is O$^-$.

39. The modified nucleoside of claim 37, wherein Z$^2$ is CH$_3$.

40. The modified nucleoside of claim 38, wherein Cat is a metal ion.

41. The modified nucleoside of claim 39, wherein Cat is a metal ion.

42. The modified nucleoside of claim 40, wherein the metal ion is an alkali metal ion and x and y are 1.

43. The modified nucleoside of claim 41, wherein the metal ion is an alkali metal ion and x and y are 1.

44. The modified nucleoside of claim 42, wherein the alkali metal ion is sodium.

45. The modified nucleoside of claim 42, wherein the alkali metal ion is potassium.

46. The modified nucleoside of claim 43, wherein the alkali metal ion is sodium.

47. The modified nucleoside of claim 43, wherein the alkali metal ion is potassium.

48. The modified nucleoside of claim 12, wherein R$^1$ is selected from the group consisting of adenosinyl, deoxyadenosinyl, guanosinyl, deoxyguanosinyl, cytidinyl, deoxycytidinyl, thymidinyl, uridinyl, inosinyl, deoxyinosinyl and dideoxyinosinyl.

49. The modified nucleoside of claim 24, wherein R$^1$ is selected from the group consisting of adenosinyl, deoxyadenosinyl, guanosinyl, deoxyguanosinyl, cytidinyl, deoxycytidinyl, thymidinyl, uridinyl, inosinyl, deoxyinosinyl and dideoxyinosinyl.

50. The modified nucleoside of claim 36, wherein R$^1$ is selected from the group consisting of adenosinyl, deoxyadenosinyl, guanosinyl, deoxyguanosinyl, cytidinyl, deoxycytidinyl, thymidinyl, uridinyl, inosinyl, deoxyinosinyl and dideoxyinosinyl.

* * * * *